(12) United States Patent
Locke

(10) Patent No.: US 11,406,750 B2
(45) Date of Patent: Aug. 9, 2022

(54) COMPRESSION STRAIN AND NEGATIVE PRESSURE DELIVERY INDICATOR FOR A WOUND DRESSING

(71) Applicant: KCI LICENSING, INC., San Antonio, TX (US)

(72) Inventor: Christopher Brian Locke, Bournemouth (GB)

(*) Notice: Subject to any disclaimer, the term of this patent is extended or adjusted under 35 U.S.C. 154(b) by 0 days.

(21) Appl. No.: 17/045,358

(22) PCT Filed: Apr. 9, 2019

(86) PCT No.: PCT/US2019/026551
§ 371 (c)(1),
(2) Date: Oct. 5, 2020

(87) PCT Pub. No.: WO2019/199798
PCT Pub. Date: Oct. 17, 2019

(65) Prior Publication Data
US 2021/0162104 A1   Jun. 3, 2021

Related U.S. Application Data (60) Provisional application No. 62/657,335, filed on Apr. 13, 2018.

(51) Int. Cl.
A61M 1/00 (2006.01)
A61F 13/00 (2006.01)
A61F 13/02 (2006.01)

(52) U.S. Cl.
CPC ......... *A61M 1/90* (2021.05); *A61F 13/00059* (2013.01); *A61F 13/0216* (2013.01); *A61F 2013/0028* (2013.01)

(58) Field of Classification Search
CPC .................. A61M 1/90; A61M 1/732; A61M 2205/583; A61F 13/00059; A61F 13/0216;
(Continued)

(56) References Cited

U.S. PATENT DOCUMENTS

| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion in International Application No. PCT/US2019/026551, dated Jul. 12, 2019.
(Continued)

*Primary Examiner* — Susan S Su
*Assistant Examiner* — Eric Rassavong (57) ABSTRACT

An indicator configured to be attached to a wound dressing includes first and second parts. The wound dressing is configured to collapse in response to an applied negative pressure. The first and second indicator parts are configured to move relative to one another as the wound dressing is collapsed. The movement of the first and second indicator parts is configured to allow a user to easily visualize the compression of the wound dressing and monitor the application of the negative pressure to the wound dressing. A marker is provided along a top surface of the first part and a window is formed on the second part. The changes in the portion of the marker that is visible in the window as the first part is slid into or under the second part are configured to provide for easier detection of the collapse of the wound dressing by the user.

21 Claims, 6 Drawing Sheets

(58) Field of Classification Search
CPC ........ A61F 2013/0028; A61F 13/00068; A61F 13/00055
See application file for complete search history.

(56) References Cited

U.S. PATENT DOCUMENTS

| | | | |
|---|---|---|---|
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1* | 4/2006 | Bubb ...................... A61M 1/74 604/317 |
| 2010/0022990 A1 | 1/2010 | Karpowicz et al. |
| 2011/0092927 A1* | 4/2011 | Wilkes .............. A61F 13/00059 604/304 |
| 2012/0209227 A1* | 8/2012 | Dunn ...................... A61M 1/84 604/319 |
| 2014/0005618 A1 | 1/2014 | Locke et al. |
| 2014/0088527 A1* | 3/2014 | Smola .................... A61M 1/90 604/319 |
| 2014/0207092 A1* | 7/2014 | Cavanaugh, II .... A61F 13/0243 604/319 |
| 2015/0320602 A1* | 11/2015 | Locke ............... A61F 13/00017 606/213 |
| 2017/0128272 A1* | 5/2017 | Wu ........................ A61M 1/90 |
| 2017/0361045 A1 | 12/2017 | Fu et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2007/030598 A2 | 3/2007 |
| WO | WO-2007/030601 A2 | 3/2007 |

(56) References Cited

FOREIGN PATENT DOCUMENTS

| WO | WO-2009/093116 A1 | 7/2009 | |
| WO | WO-2010/053870 A1 | 5/2010 | |
| WO | WO-2010053870 A1 * | 5/2010 | ........... A61B 17/085 |
| WO | WO-2014/140578 A1 | 9/2014 | |
| WO | WO-2018/033794 A1 | 2/2018 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, Nos. May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sept. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu .A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

COMPRESSION STRAIN AND NEGATIVE PRESSURE DELIVERY INDICATOR FOR A WOUND DRESSING

CROSS-REFERENCE TO RELATED APPLICATIONS

This application claims the benefit of priority to international application PCT/US2019/026551, filed Apr. 9, 2019, and U.S. Provisional Application No. 62/657,335, filed on Apr. 13, 2018, the complete disclosures of which are hereby incorporated herein by reference in their entireties.

BACKGROUND

The present disclosure relates generally to an indicator for a negative pressure wound therapy ("NPWT") system, and more particularly to an indicator configured to provide visual indication to a user related to the amount of negative pressure applied to a wound site and the degree of wound dressing collapse during a NPWT treatment.

Negative pressure wound therapy is a type of wound therapy that involves applying negative pressure via a pump unit to a wound dressing that has been applied over a wound site. NPWT may promote wound healing by using the pump unit to create a vacuum within the wound dressing overlaying the wound site, causing the removal of wound exudate, air, and other fluids from the wound site.

The wound dressing used in a NPWT system may advantageously include a three-dimensional, absorbent foam layer, such that upon application of negative pressure to the wound dressing, the wound dressing is compressed in a lateral, longitudinal, and/or vertical direction. Accordingly, in addition to promoting wound healing via the removal of wound exudate, air, and other fluids from the wound site, the compression strain imparted by the wound dressing on a wound during NPWT treatment may provide the additional benefit of aiding in contracting the wound.

Given the benefits of applying negative pressure to a wound site and the beneficial role wound dressing compression during NPWT may play in the wound treatment process, it would be desirable to provide a simple, inexpensive and easy to install tool by which a user can monitor the amount and progress of negative pressure delivery to a wound site and/or the degree of wound dressing collapse during NPWT treatment. Such a visualization tool would allow a user to quickly confirm the status of NPWT treatment, monitor the degree of the collapse of the wound dressing, measure the amount of negative pressure applied to the wound site, be reminded of the benefits of the NPWT treatment and/or be alerted to potential problems with the NPWT treatment.

SUMMARY

One implementation of the present disclosure is a negative pressure wound therapy system including a wound dressing and an indicator. The wound dressing is sealable to a patient's skin surrounding a wound. The wound dressing is configured to laterally collapse upon application of negative pressure to the wound dressing. The indicator is coupled to the wound dressing and is configured to visually indicate an amount by which the wound dressing laterally collapses upon the application of negative pressure.

In some embodiments, the wound dressing includes a first lateral side and a second lateral side opposite the first lateral side. The amount by which the wound dressing laterally collapses is an amount by which a distance between the first lateral side and the second lateral side decreases upon the application of negative pressure.

In some embodiments, the indicator includes a first part coupled to a first lateral side of the wound dressing and a second part coupled to a second lateral side of the wound dressing opposite the first lateral side. The first and second parts of the indicator extend along a top surface of the wound dressing and at least partially overlap with each other along the top surface. The first and second parts of the indicator are slidably connected along a top surface of the wound dressing such that the first part slides under or into the second part when the wound dressing laterally collapses.

In some embodiments, the first part of the indicator includes a marker on a top surface of the first part and the second part of the indicator includes a window through which the marker is at least partially visible when the first part slides under or into the second part. The window has a length between approximately 5 mm and approximately 15 mm measured laterally along the top surface of the wound dressing. In some embodiments, the window has a width of approximately 10 mm measured longitudinally along the top surface of the wound dressing.

In some embodiments, the window is surrounded on all sides by the second part of the indicator. An edge of the window is collinear with an edge of the second part of the indicator such that the window forms a notch extending into the second part from the edge.

In some embodiments, the first and second parts of the indicator are configured to move relative to each other as the wound dressing laterally collapses such that a different portion of the marker is visible through the window based on an amount by which the wound dressing has laterally collapsed.

In some embodiments, the marker includes a colored scale having a plurality of colored bands. The one or more of the colored bands are visible through the window based on an amount by which the wound dressing has laterally collapsed. Each of the colored bands corresponds to an amount of negative pressure and indicates the amount by which the wound dressing laterally collapses when the corresponding amount of negative pressure is applied to the wound dressing. The plurality of colored bands includes a first colored band corresponding to a negative pressure of less than 50 mmHg. The wound dressing is configured to laterally collapse by a first amount such that the first colored band is visible through the window when the negative pressure applied to the wound dressing is less than 50 mmHg.

In some embodiments, plurality of colored bands includes a second colored band corresponding to a negative pressure between 50 mmHg and 125 mmHg. The wound dressing is configured to laterally collapse by a second amount such that the second colored band is visible through the window when the negative pressure applied to the wound dressing is between 50 mmHg and 125 mmHg.

In some embodiments, the plurality of colored bands includes a third colored band corresponding to a negative pressure of at least 125 mmHg. The wound dressing is configured to laterally collapse by a third amount such that the third colored band is visible through the window when the negative pressure applied to the wound dressing is at least 125 mmHg.

In some embodiments, the marker includes a plurality of lines of text. One or more of the lines of text are visible through the window based on an amount by which the wound dressing has laterally collapsed.

In some embodiments, the marker includes a gradient of lines. One or more of the lines are visible through the window based on an amount by which the wound dressing has laterally collapsed.

In some embodiments, the marker includes a triangular shape. A different portion of the triangular shape is visible through the window based on an amount by which the wound dressing has laterally collapsed.

In some embodiments, the wound dressing includes a longitudinal dimension and a lateral dimension perpendicular to the longitudinal dimension. The wound dressing is configured to hold edges of the wound together by collapsing along the lateral dimension of the wound dressing.

In some embodiments, the wound is an incision wound. The wound dressing is configured to be applied to a patient's skin around the incision wound such that the longitudinal dimension aligns with the incision wound.

In some embodiments, the wound dressing includes a foam layer having a first side and a second wound-facing side and a backing layer having a first side and a second wound-facing side abutting the first side of the foam layer. The backing layer is substantially impermeable to air and configured to maintain the negative pressure applied to the wound dressing.

In some embodiments, the indicator is positioned between the foam layer and the backing layer. In some embodiments, the indicator is coupled to the first side of the backing layer such that the backing layer is positioned between the indicator and the foam layer.

In some embodiments, the indicator is detachable from the wound dressing. In some embodiments, the indicator is coupled to the wound dressing via one or more perforated sections that facilitate detaching the indicator from the wound dressing.

One implementation of the present disclosure is a method for monitoring the status of a negative pressure wound therapy treatment. The method includes applying a wound dressing to a patient's skin surrounding a wound. The wound dressing includes an indicator configured to indicate to a user whether there has been a change in at least one of a lateral or a longitudinal dimension of the wound dressing. A source of negative pressure is applied to the wound dressing. A change in at least one of the lateral or the longitudinal dimensions of the wound dressing is observed on the indicator.

In some embodiments, the wound dressing is configured to collapse in at least a lateral direction such that a second lateral dimension of the wound dressing following the application of negative pressure is less than a first lateral dimension of the wound dressing prior to the application of negative pressure.

In some embodiments, the indicator includes a first part coupled to a first lateral side of the wound dressing and a second part coupled to a second lateral side of the wound dressing opposite the first lateral side. Observing the change in at least one of the lateral or the longitudinal dimensions of the wound dressing includes monitoring movement of one or both of the first part or the second part of the indicator following the application of negative pressure to the wound dressing.

In some embodiments, the detection of movement of one or both of the first part or the second part of the indicator is configured to indicate a collapse of the wound dressing in the lateral direction. The lack of any movement of one or both of the first part or the second part of the indicator in response to the application of negative pressure is configured to indicate an issue with the negative pressure wound therapy treatment.

In some embodiments, a connection between the wound dressing and a pressure source configured apply a negative pressure to the wound dressing is verified in response to no movement of either the first part or the second part of the indicator relative to one another being observed.

In some embodiments, the first and second parts of the indicator extend along a top surface of the wound dressing and at least partially overlap with each other along the top surface. The first and second parts of the indicator are slidably connected along a top surface of the wound dressing such that the first part slides under or into the second part when the wound dressing laterally collapses.

In some embodiments, the first part of the indicator includes a marker on a top surface of the first part and the second part of the indicator includes a window through which the marker is at least partially visible when the first part slides under or into the second part. The first and second parts of the indicator are configured to move relative to each other as the wound dressing laterally collapses such that a different portion of the marker is visible through the window based on an amount by which the wound dressing has laterally collapsed.

In some embodiments, the wound dressing is configured to hold edges of the wound together by collapsing along the lateral dimension of the wound dressing. The wound may be an incision wound and the wound dressing is configured to be applied to a patient's skin around the incision wound such that the longitudinal dimension aligns with the incision wound.

In some embodiments, the wound dressing includes a foam layer and a backing layer. The layer has a first side and a second wound-facing side. The backing layer has a first side and a second wound-facing side abutting the first side of the foam layer. The backing layer is substantially impermeable to air and is configured to maintain the negative pressure applied to the wound dressing. The indicator is coupled to the first side of the backing layer such that the backing layer is positioned between the indicator and the foam layer.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
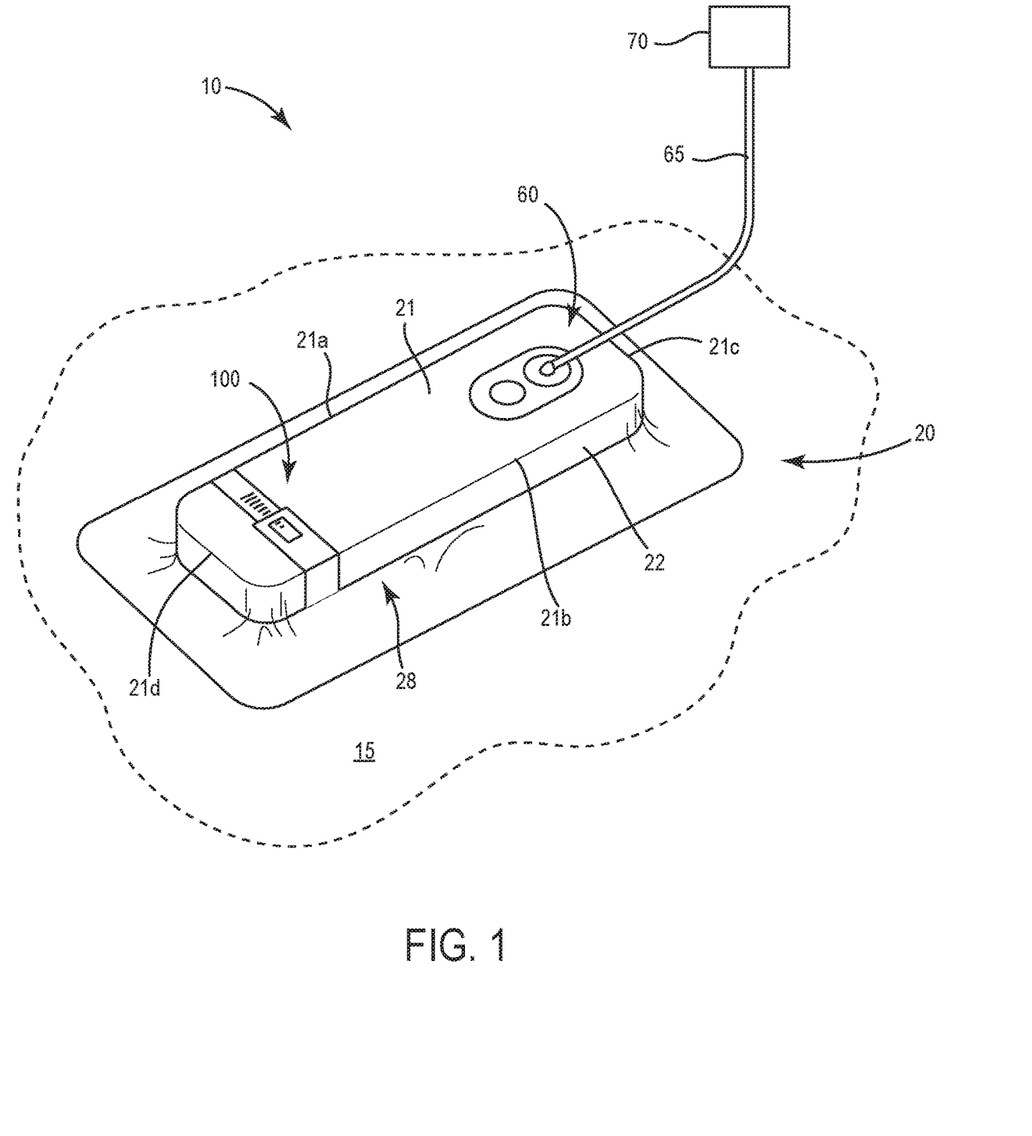
FIG. 1 is a top perspective view of a negative pressure wound therapy system having an attached indicator, according to an exemplary embodiment.
Figure 2:
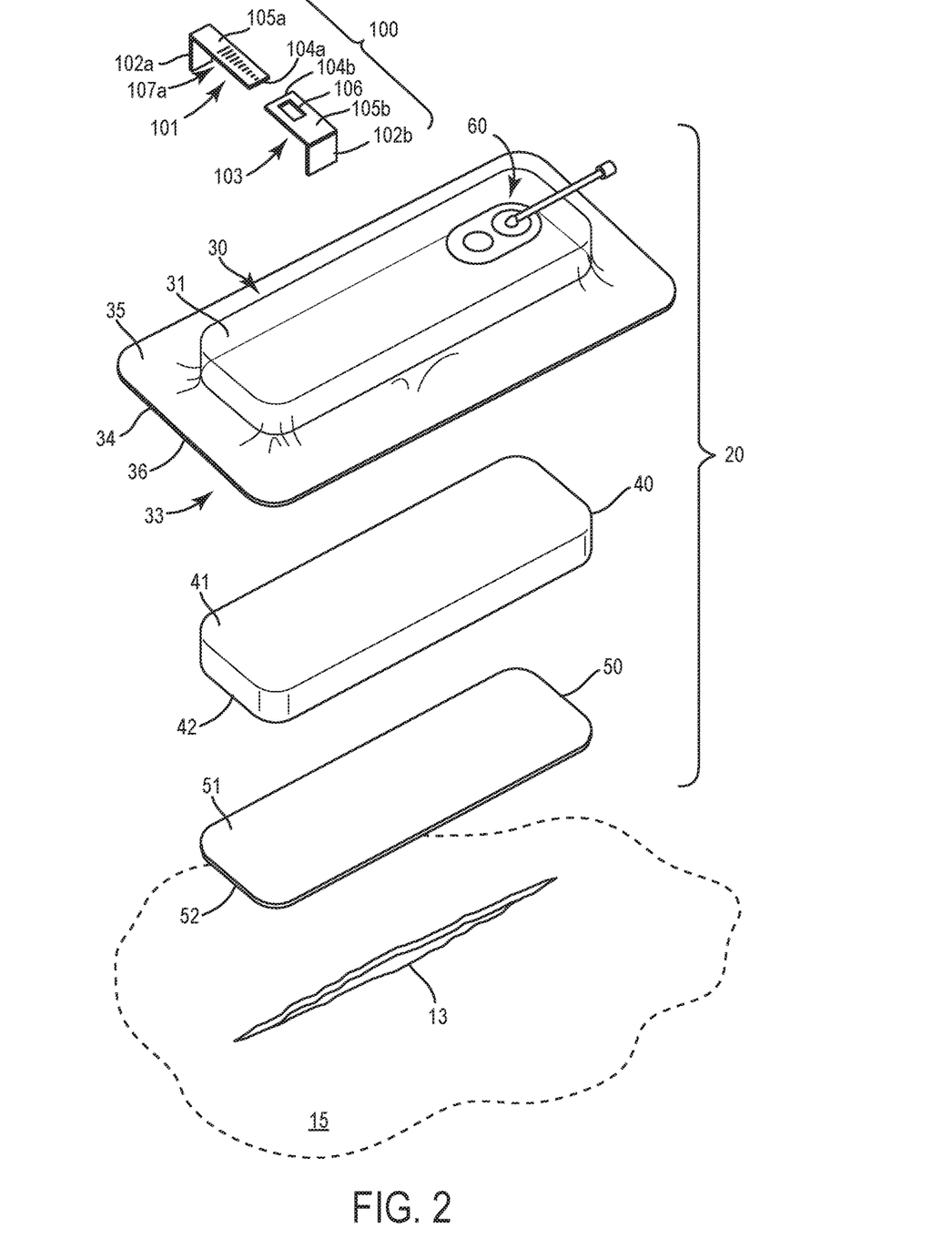
FIG. 2 is an exploded perspective view of the wound dressing and indicator of the negative pressure wound therapy system of FIG. 1, according to an exemplary embodiment.

Referring to FIGS. 1 and 2, a negative pressure wound therapy ("NPWT") system 10 having an attached indicator 100 is shown according to one embodiment. As illustrated in FIG. 1, the NPWT system 10 generally includes a wound dressing 20 configured to be applied to a patient's skin 15 around the wound site that is to be treated and a therapy unit 70 configured to apply a negative pressure to the wound site during the NPWT treatment. While the amount and nature of the negative pressure applied to the wound site can vary, the pressure typically applied by the therapy unit 70 to the wound dressing 20 is within a range of approximately negative 5 mm Hg and approximately negative 500 mm Hg and more typically within a range of approximately negative 100 mm Hg and approximately negative 300 mm Hg.

The wound dressing may advantageously incorporate an absorbent, three-dimensional foam layer 40. The incorporation of such a foam layer 40 allows the wound dressing 20 to deform and collapse inwards as a result of the negative pressure applied during NPWT treatment. This compressive strain experienced by the wound dressing 20 may be imparted onto the edges of the wound 13, providing a closing force that assists in contracting the wound 13 and expediting the wound healing process.

Given the beneficial role that the collapse of the foam layer 40 during NPWT treatment may play in assisting in wound contraction, it may be desirable to provide the NPWT system 10 with an indicator 100 that allows a user, such as e.g., a medical practitioner or patient, to more easily detect, observe and/or confirm the collapse of the wound dressing 20.

In addition to providing a user with a representative visualization of the collapse of the wound dressing 20 and the progress of the NPWT treatment, the indicator 100 may also be useful in gauging whether a desired or appropriate amount of negative pressure has been applied to the wound dressing 20. For example, the failure of the indicator 100 to show that there has been a desired degree of—or any— collapse of the wound dressing 20 may indicate to a user the desired amount of negative pressure has not been delivered to the wound dressing 20. Accordingly, the indicator 100 may also assist in alerting a user to potential issues (e.g. a leak in the wound dressing, a full canister, blockage in the tubing) with the NPWT system 10.

NPWT System

A NPWT system 10 according to any number of various embodiments may be used with the indicator 100 described herein. The indicator 100 can be used with NPWT systems 10 adapted to treat any number of different types of wounds, including wounds defined by any number of different shapes, sizes and configurations. As illustrated in FIG. 2, in some embodiments, the wound 13 may comprise an incision wound.

Illustrated in FIGS. 1 and 2 is a representative NPWT system 10 with which an indicator 100 may be used. In general, as illustrated in the exemplary NPWT system 10 of FIG. 1, the NPWT system 10 may include a wound dressing 20 and a therapy unit 70. One example of a NPWT system 10 that may be used with an indicator 100 as disclosed herein is the PREVENA™ Incision Management System that is available from Kinetic Concepts, Inc. (KCI) of San Antonio, Tex.

Wound Dressing

As shown in the exploded perspective view of FIG. 2, the wound dressing 20 generally comprises an impermeable backing layer 30 and an absorbent, three-dimensional foam layer 40. In some embodiments, the wound dressing may optionally also include a non-adherent layer 50.

An outer surface of the wound dressing 20 may be defined by the upper surface 35 of the margin 34 and the upper surface 31 of the backing layer 30. As illustrated in FIG. 1, in an assembled configuration, a portion the wound dressing 20 may be defined by a three-dimensional structure 28 within which the foam layer 40 and, if included, non-adherent layer 50 may be located. The three-dimensional structure includes an upper surface 21 and a vertically extending sidewall 22 that extends downwards from the outer perimeter of the upper surface 21 of the three-dimensional structure 28. The outer perimeter of the upper surface 21 is defined by a first lateral side 21a, a second lateral side 21b, a top end 21c, and a bottom end 21d.

The wound dressing 20 may be substantially planar or may be contoured for application to body surfaces having high curvature. The size of wound dressing 20 can vary depending on the size of the wound to be dressed. For example, it is contemplated that the size of wound dressing 20 can be within a range of approximately 200 cm² to approximately 1,000 cm², and more preferably within a range of approximately 400 cm² to approximately 700 cm². However, other shapes and sizes of wound dressing 20 are also possible depending on intended use.

i. Backing Layer

Referring to FIG. 2, the backing layer 30 includes a first, upper surface 31 and a second, wound-facing surface 32 opposite the first surface 31. The backing layer 30 is configured to maintain a vacuum within the wound dressing 20 upon application of negative pressure to the wound dressing 20. The backing layer 30 may be substantially impermeable to liquid and substantially permeable to water vapor. In some embodiments, the backing layer 30 is also impermeable to bacteria and other microorganisms.

As non-limiting examples, the backing layer 30 may be formed from materials that include a silicone, 3M Tegaderm® drape material, acrylic drape material such as one available from Avery, or an incise drape material.

The backing layer 30 may define a cavity 33 for receiving the foam layer 40 and, if included, the non-adherent layer 50. As shown in FIG. 2, the cavity 33, the foam layer 40 and the non-adherent layer 50 may have a similar perimeter or profile.

Provided along and extending through the backing layer 30 from the first surface 31 to the second surface 32 may be at least one access point through which negative pressure can be applied to the interior of the wound dressing 20 once the wound dressing 20 has been applied to the desired wound site. As illustrated in FIGS. 1 and 2, in some embodiments, the access point may comprise a port and tubing connector assembly 60 (e.g. SENSAT.R.A.C.™ Pad available from Kinetic Concepts, Inc. (KCI) of San Antonio, Tex., etc.) configured to be fluidly sealed to a fluid conduit 65 of the therapy unit 70.

ii. Margin

An adhesive-coated margin 34 for adhering the wound dressing 20 to a patient's skin 15 adjacent the wound 13 being treated may extend outwards from the perimeter of backing layer 30. The margin 34 includes a first, upper surface 35 and a second, wound-facing surface 36. An adhesive is applied along the wound-facing surface 36 of the margin 34, and is intended to ensure that the wound dressing 20 adheres to the surface of the patient's skin 15 and remains in place during the NPWT treatment.

As illustrated in FIGS. 1 and 2, in some embodiments, the margin 34 may be formed integrally, or even monolithically, with the backing layer 30. In other embodiments, the adhesive-coated margin 34 can be eliminated, and wound dressing 20 can be adhered to a patient's skin 15 using other techniques.

iii. Foam Layer

Referring to FIG. 2, the foam layer 40 includes a first, upper surface 41 and a second, wound-facing surface 42 opposite the first surface 41. The foam layer 40 is formed from an absorbent material and is adapted to wick fluid (e.g. exudate) from the wound 13.

Any material or combination of materials may be used for the foam layer 40 provided that the foam layer 40 is operable to distribute the reduced pressure and provide a distributed compressive force along the wound site during NPWT treatment. One non-limiting example of a foam material that may be used is the V.A.C.® Granufoam™ material that is available from Kinetic Concepts, Inc. (KCI) of San Antonio, Tex.

iv. Non-Adherent Layer

In some embodiments, wound dressing 20 may optionally include a non-adherent layer 50. As shown in FIG. 2, non-adherent layer 50 includes a first, upper side 51 and a second, wound-facing side 52 opposite first side 51. As the wound-facing side 52 is configured to contact the wound 13 over which wound dressing 20 is applied, the non-adherent layer 50 may function as a contact layer providing an interface between wound dressing 20 and the wound 13.

Non-adherent layer 50 may be advantageous in fibrinous situations to reduce potential adherence of the foam layer 40 to the wound 13. In some embodiments, non-adherent layer 50 is made of a hydrophobic material such as polyethylene (PE) or other hydrophobic polymers. The use of a hydrophobic material for non-adherent layer 50 may be particularly advantageous to prevent the attachment of bacteria to the wound or tissue site. In some embodiments, non-adherent layer 50 is perforated for increased fluid flow.

In some embodiments, the perimeter of non-adherent layer 50 extends beyond the perimeter of foam layer 40 such that a portion of the perimeter of the non-adherent layer 50 contacts the wound-facing surface 36 of the adhesive-coated margin 34. In such a manner, the non-adherent layer 50 and cavity 33 defined by the backing layer 30 may be used to form a closed pocket within which the foam layer 40 may be contained, which may facilitate the placement of the wounding dressing 20 at the wound site.

Therapy Unit

The NPWT system may include a therapy unit 70 comprising a removed-fluid container (e.g. canister, etc.) and a pump. The operation of the pump is configured to subject the wound site to negative pressure and the canister is adapted to store a fluid removed from the wound site (e.g., wound exudate, etc.). The therapy unit 70 may be fluidly coupled to the wound dressing 20 via a fluid conduit 65 attached to the port and tubing connector assembly 60 attached to the backing layer 30. One non-limiting example of therapy units 70 that may be used are the V.A.C.® products that are available from Kinetic Concepts, Inc. (KCI) of San Antonio, Tex.

NPWT Treatment

In various embodiments, NPWT treatment may begin with the wound dressing 20 being applied to the patient's skin 15 at a desired wound site. The wound dressing 20 may be attached to the patient's skin 15 at any desired orientation relative to the wound 13. As illustrated in FIG. 2, in various embodiments, the wound dressing 20 may be applied to the patient's skin 15 with the length, or longitudinal direction, of the wound dressing 20 extending generally parallel to and aligning with the length of the wound 13.

Following the securement of the wound dressing 20 to the patient's skin 15, the fluid conduit 65 may be attached to the port and tubing connector assembly 60 extending from the backing layer 30. Once attached, the therapy unit 70 may be operated to apply a negative pressure to the wound dressing 20.

Figure 3A:
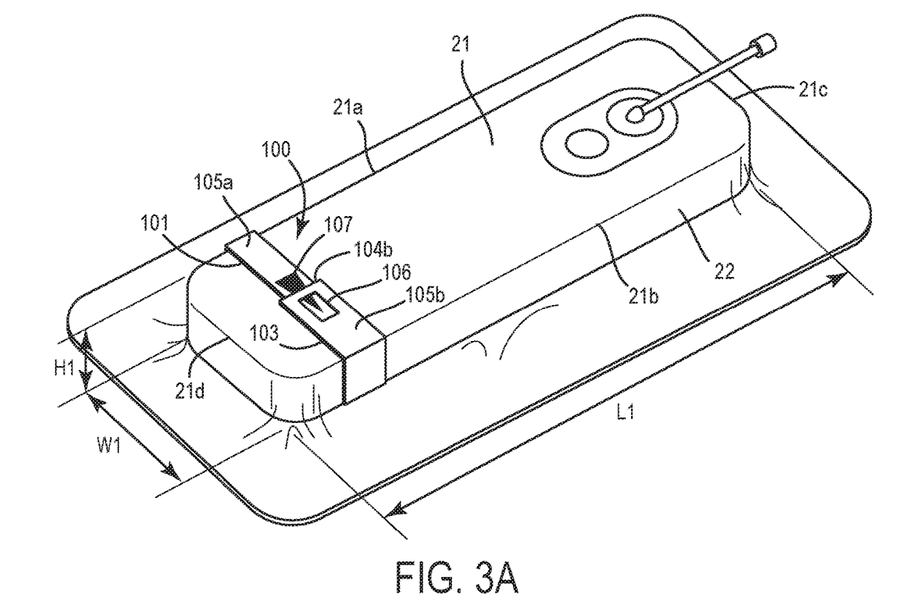
FIG. 3A is a top perspective view of a wound dressing having an attached indicator in an initial, uncompressed configuration, according to an exemplary embodiment.
Figure 3B:
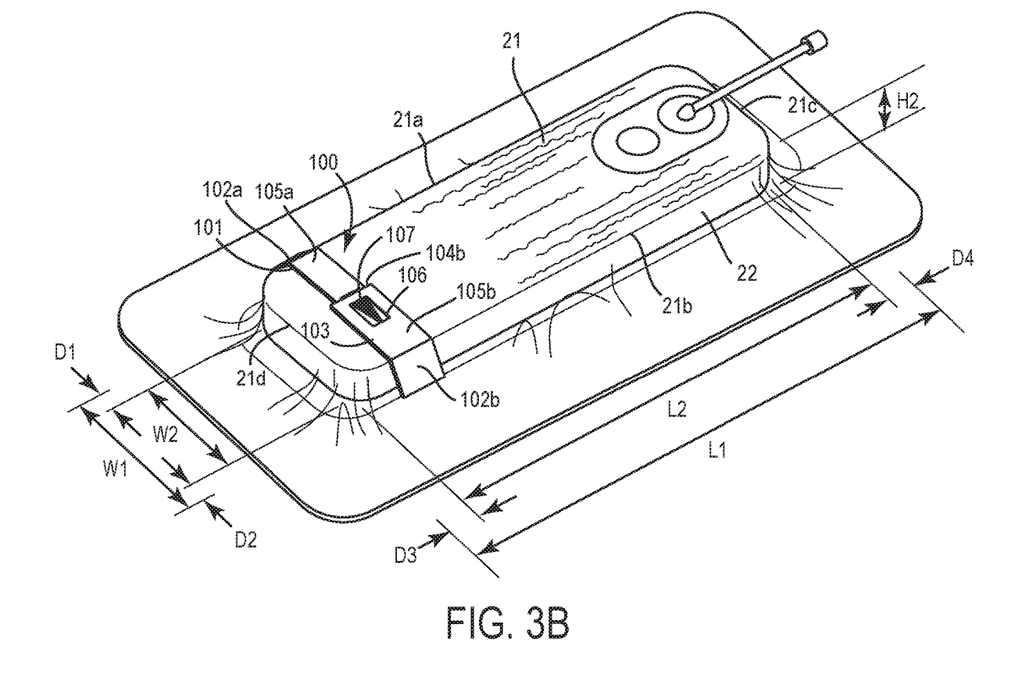
FIG. 3B is a top perspective view of the wound dressing and attached indicator of FIG. 3A in a compressed configuration, according to an exemplary embodiment.

Referring to FIGS. 3A and 3B, the application of negative pressure to the foam-based wound dressing 20 during NPWT treatment is configured to cause a lateral, longitudinal, and/or vertical collapse of the wound dressing 20. As shown in FIG. 3A, in an initial, pre-treatment configuration of the wound dressing 20, the first lateral side 21a and the second lateral side 21b of the wound dressing 20 are separated by a distance W1, the top end 21c and the bottom end 21d of the wound dressing 20 are separated by a distance L1, and the vertically extending sidewall 22 is defined by a height H1.

Illustrated in FIG. 3B is the wound dressing 20 of FIG. 3A following the application of negative pressure to the wound dressing 20. As shown in FIG. 3B, as a result of the applied negative pressure, the first lateral side 21a and the second lateral side 21b of the wound dressing 20 may collapse inwards by distances of D1 and D2, respectively. Accordingly, following the application of negative pressure, the first lateral side 21a and the second lateral side 21b of the wound dressing 20 may be separated by a distance W2 which is less than the initial separation distance W1.

As further illustrated in FIG. 3B, upon application of negative pressure, the top end 21c and the bottom end 21d of the wound dressing 20 may collapse inwards by distances D3 and D4, respectively. Accordingly, following the application of negative pressure, the top end 21c and the bottom end 21d of the wound dressing 20 may be separated by a distance L2 which is less than the initial separation distance L1.

Continuing to refer to FIG. 3B, upon application of negative pressure, the wound dressing 20 may also collapse along the vertical dimension, such that following the application of negative pressure, the vertically extending sidewall 22 of the wound dressing 20 has a height H2 which is less than the initial height H1.

The degree of collapse of the wound dressing 20 in the longitudinal, lateral and/or vertical directions may be related to and controlled via the selection of materials and configurations used to construct foam layer 40. Accordingly, although in the embodiment of FIGS. 3A and 3B, the wound dressing 20 is shown as exhibiting collapse in each of the lateral, longitudinal and vertical directions following the application of negative pressure, it is to be understood that in other embodiments the wound dressing 20 may be configured to exhibit collapse in only one of the lateral, longitudinal and/or vertical dimensions. Similarly, although in FIGS. 3A and 3B the wound dressing 20 is shown as collapsing symmetrically about both the longitudinal and lateral axes, in other embodiments the wound dressing 20 may be configured so as to allow for asymmetrical collapse of the wound dressing 20 about the longitudinal and/or lateral axes.

Indicator

Given the various benefits that the compression of a wound dressing 20 during a NPWT treatment may provide in the treatment of a wound site, it may be advantageous to provide a user with an indicator 100 that may draw the user's attention to the collapse of the wound dressing 20 during NPWT treatment, and which may also allow the user to more easily detect and monitor the negative pressure applied to the wound dressing 20 and the progress of the NPWT treatment.

Illustrated in FIGS. 3A and 3B is one embodiment of an indicator 100 that may be used with a NPWT system 10. As shown in FIGS. 3A and 3B, in various embodiments the indicator 100 includes a first part 101 and a second part 103. Each of the first and second parts 101, 103 of the indicator 100 include an attachment end 102a, 102b, a free end 104a, 104b, and a body portion 105a, 105b connected to and extending between the attachment end 102a, 102b and free end 104a, 104b.

The attachment ends 102a, 102b of the first and second parts 101, 103 are adapted to be mounted to the wound dressing 20, while the body portions 105a, 105b and free ends 104a, 104b of the first and second parts 101, 103 remain detached from the wound dressing 20. The attachment ends 102a, 102b of the indicator 100 may be attached to the wound dressing 20 using any number of known attachments, such as e.g., an adhesive applied along the bottom surfaces of the attachment ends 102a, 102b and/or along an outer surface of the wound dressing 20.

As shown in FIGS. 3A and 3B, in various embodiments, the attachment ends 102a, 102b of each of the first and second parts 101, 103 of the indicator 100 are coupled to the wound dressing 20 along the sidewall 22 of the three-dimensional structure 28 of the wound dressing 20. In other embodiments, such as, e.g. illustrated in FIGS. 4A and 4B, the attachment ends 102a, 102b of the first and second parts 101, 103 of the indicator 100 may be coupled to the upper surface 21 of the three-dimensional structure 28 of the wound dressing 20.

In general, the attachment of the indicator 100 relative to the wound dressing 20 is oriented such that the first and second parts 101, 103 of the indicator 100 lie substantially parallel to the desired direction of the wound dressing 20 collapse that the user wishes to observe. In situations in which a user wishes to observe the progress of the contraction of a wound 13, the first and second parts 101, 103 of the indicator 100 may be arranged in a direction generally perpendicular to the length of the wound 13 (i.e. perpendicular to the direction of wound contraction). Accordingly, in embodiments in which a longitudinal dimension of a wound dressing 20 is aligned with a length of a wound 13, such as e.g. illustrated in FIGS. 1 and 2, the orientation of the first and second parts 101, 103 of the indicator 100 perpendicular relative to the longitudinal dimension of the wound dressing 20 may enable the user to visualize and monitor the contraction of the wound 13 during NPWT treatment.

In various embodiments, the first and second parts 101, 103 of the indicator 100 are arranged collinearly, with the free end 104a of the first part 101 being adapted to slide under the free end 104b of the second part 103, or into a pocket defined by the free end 104b and body portion 105b of the second part 103. In such embodiments, the dimensions of the body portions 105a, 105b of the first and second parts 101, 103 of the indicator 100 may be chosen to ensure that, as the wound dressing 20 collapses, the free ends 104a, 104b of the first and second parts 101, 103 will overlap. As representatively illustrated by FIGS. 3A/3B and 4A/4B, in various embodiments, the dimensions of the body portions 105a, 105b of the first and second parts 101, 103 may advantageously be dimensioned such that, even in an initial, uncompressed wound dressing configuration 20 (such as illustrated e.g. in FIGS. 3A and 4A), the free end 104a of the first part 101 is positioned under or within a pocket defined by the second part 103 of the indicator 100, so as to avoid or minimize the possibility that the first part 101 does not slide under or into the body portion 105b of the second part 103 as intended.

Figure 4A:
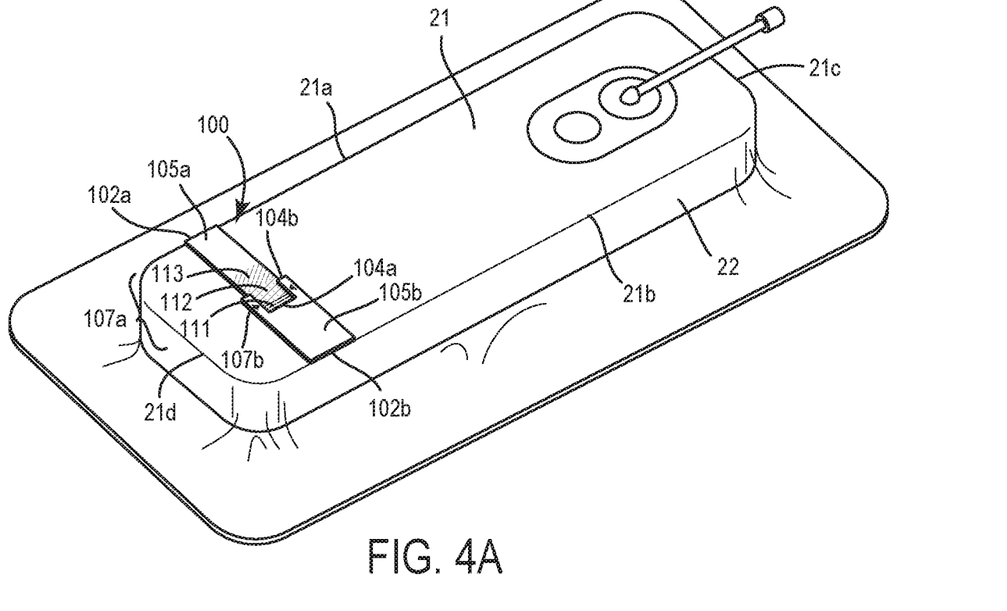
FIG. 4A is a top perspective view of a wound dressing having an attached indicator in an initial, uncompressed configuration, according to an exemplary embodiment.
Figure 4B:
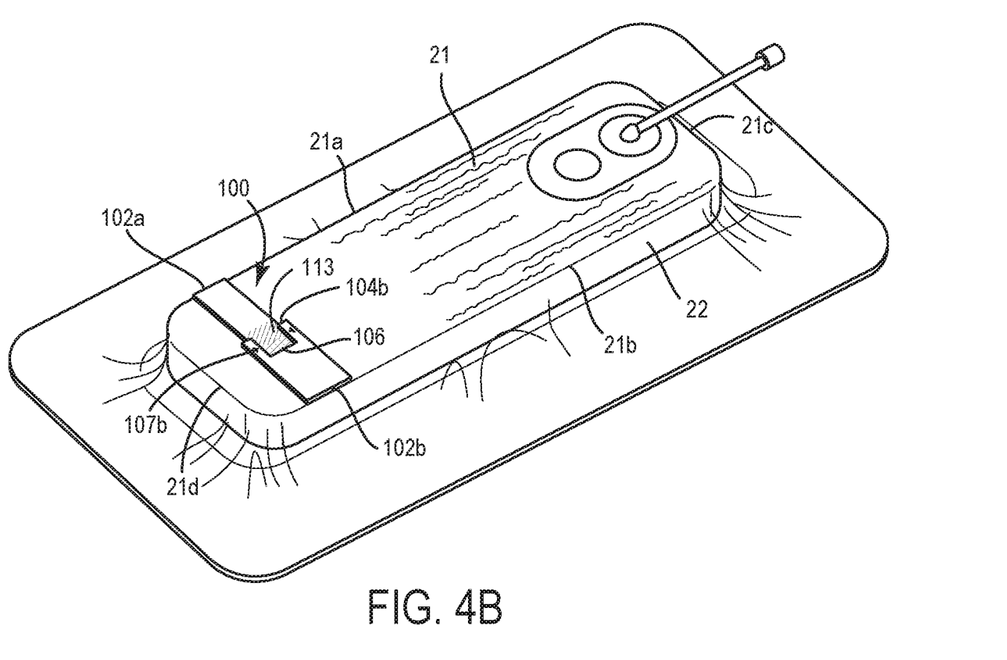
FIG. 4B is a top perspective view of the wound dressing and attached indicator of FIG. 4A in a compressed configuration, according to an exemplary embodiment.

In indicator 100 embodiments in which the first and second parts 101, 103 of the indicator 100 are adapted to be arranged collinearly, the body portion 105b of the second part 103 may optionally include a window 106 through which an upper surface of the body portion 105a of the first part 101 may be visible. As shown by the indicator 100 embodiment of FIGS. 3A and 3B, in some embodiments the window 106 formed in the second part 103 of the indicator 100 may be surrounded on all sides by the body portion 105b of the second part 103. Alternatively, as illustrated by FIGS. 4A and 4B, in other embodiments an edge of the window 106 may instead be formed collinear with the edge of the free end 104b of the second part 103, such that the window 106 forms a notch that extends into the body portion 105b of the second part 103 of the indicator 100.

In those indicator 100 embodiments incorporating a window 106, the window 106 may be formed having any size or shape as desired. In some embodiments, the window 106 may have a length within a range of approximately 5 mm and approximately 15 mm as measured between first and second side edges 106a, 106b of the window 106. In some embodiments, the window 106 may have a width of approximately 10 mm as measured between the upper and lower edges 106c, 106d of the window 106.

To facilitate the visualization of, and optionally the degree of, the collapse of the wound dressing 20 during NPWT treatment, the indicator 100 may optionally include one or more markers 107 formed about all of or a portion of the top surface the indicator 100. As illustrated by the representative indicator 100 embodiments depicted in FIGS. 3-6, the one or more markers 107 may comprise any number of designs, and may be formed in any number of arrangements about the top surfaces of one or both of the first and second parts 101, 103 of the indicator 100.

In indicator 100 embodiments in which the first and second parts 101, 103 are arranged collinearly, the incorporation of a marker 107a formed on the upper surface of the body portion 105a of the first part 101 may allow a user to more easily detect and observe movement of the first and second parts 101, 103 relative to one another. More specifically, as the wound dressing 20 is compressed, the change in the portion of the marker 107a that remains visible as the first part 101 slides into or under the second part 103 may provide an easy and quick way by which a user can confirm that the NPWT treatment has begun. Advantageously, the incorporation of a window 106 on the second part 103 of the indicator 100 may help draw a user's attention to the changes in the portions of the marker 107a that remain visible, thereby further increasing the ease with which a user can detect the collapse of the wound dressing 20.

Depicted in FIGS. 3-6 are various representative embodiments of different types of markers 107 that may be formed on one or both of the first and second parts 101, 103 of the indicator 100. As illustrated in FIGS. 3A and 3B, in some embodiments the marker 107a may define a triangular shape arranged such that a point of the triangle is located adjacent the free end 104a of the first part 101 and the base of the triangle is located adjacent the attachment end 102a of the first part 101. Illustrated in FIGS. 4A and 4B is a marker 107a embodiment incorporating a plurality of colored bands. As shown in FIGS. 5A and 5B, in some embodiments, the marker 107 may comprise a plurality of lines of text formed between the attachment end 102a and the free end 104a of the first part 101. In other embodiments, as e.g. illustrated by FIGS. 6A and 6B, the marker 107 may comprise a plurality of gradient lines.

In various embodiments, the arrangement of the one or more markers 107 about the top surface of the indicator 100 may be adapted to not only signal to a user that there has been a collapse of the wound dressing 20, but may also additionally be adapted to provide an indication to the user as to the degree of the progress of the NPWT treatment and/or the amount of pressure that has been applied to the wound dressing 20. In such embodiments, the spacing and arrangement of the marker 107 between the free end 104a and attachment end 102a of the first part 101 may be selected and calibrated to correspond to specific pressures and/or stages of the NPWT treatment.

For example, in the embodiment of FIGS. 3A and 3B, the location of the tip of the triangle on the top surface of the first part 101 may correspond to the portion of the top surface of the first part 101 that will be visible through the window 106 when the wound dressing 20 is in an initial, uncompressed configuration, such as illustrated in FIG. 3A. Meanwhile, the base of the triangle may be formed about the portion of the upper surface of the first part 101 that will be visible through the window 106 when the wound dressing 20 has been compressed to a predetermined, desired degree, as representatively illustrated in FIG. 3B.

Turning to FIGS. 4A and 4B, in some embodiments, the color of a band that is visible in the window of the indicator may be used communicate to a user the progress of the NPWT treatment. According to one embodiment, a marker 107 comprising a plurality of colored bands may include a green band 111, a yellow band 112, and a red band 113. The red band 113 may be positioned adjacent the free end 104a of the first part 101 such that, when the wound dressing 20 is in an initial, uncompressed state, the red band 113 is visible through the window 106 of the second part 103. The green band 111 may be positioned adjacent the attachment end 102a of the first part 101 such that, when the wound dressing 20 has been compressed by a desired, predetermined amount, the green band 111 is visible in the window 106 of the second part 103. In such an embodiment, the presence of the red band 113 in the window 106 may signal to a user that the NPWT treatment has not yet progressed by a desired amount, whereas the presence of the green band 111 in the window 106 may indicate to the user that the NPWT treatment is progressing as intended.

In other embodiments, the spacing and arrangement of the colored bands 111, 112, and 113 may be representative of the amount of negative pressure that has been applied to the wound dressing 20. For example, a first band may be representative of a negative pressure of less than approximately 50 mmHg, a second band may be representative of a negative pressure within a range of approximately 50 mmHg and approximately 125 mmHg, and a third band may be representative of a negative pressure of at least approximately 125 mmHg.

The bands 111, 112, and 113 may be spaced along the upper surface of the first part 101 such that, in response to a negative pressure of less than 50 mmHg being applied to the wound dressing 20, the wound dressing 20 collapses laterally by a first amount, resulting in the first band 111 being visible in the window 106. In response to a negative pressure of between 50 mmHg and 125 mmHg being applied to the wound dressing 20, the wound dressing 20 collapses laterally by a second amount, resulting in the second band 112 being visible in the window 106. In response to a negative pressure of at least 125 mmHg being applied to the wound dressing 20, the wound dressing 20 collapses laterally by a third amount, resulting in the third band 113 being visible in the window 106.

Depending on the portions of the wound dressing 20 to which the attachment ends 102a, 102b of the first and second parts 101, 103 of the indicator 100 are coupled, the collapse of the wound dressing 20 during NPWT treatment may result in the free ends 104a, 104b of the first and second parts 101, 103 of the indicator 100 each moving inwards relative to one another, or may result in only one of the free ends 104a, 104b of the first and second parts 101, 103 of the indicator 100 being moved relative to the free end 104b, 104a of the other of the first and second parts 101, 103. Given that the amount of displacement between the free ends 104a, 104b of the first and second parts 101, 103 may vary based on the locations to which the attachment ends 102a, 102b of the indicator 100 are attached, the spacing and arrangement of a marker 107 along the indicator 100 may need to be adjusted to ensure that the degree of movement of the mark 107 and the portion of the marker 107 that is visible as negative pressure is applied accurately represents the degree of NPWT treatment progress and/or the amount of pressure applied to the wound site.

Figure 5A:
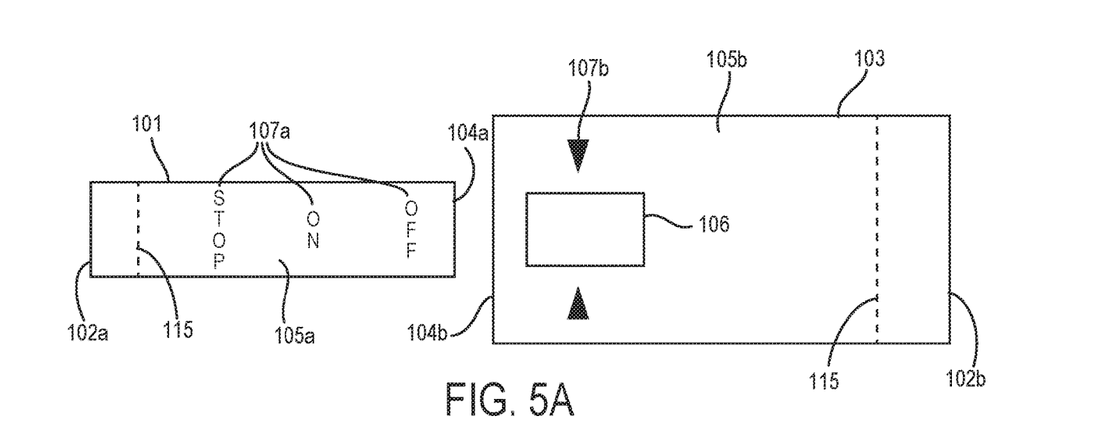
FIG. 5A is a top view of an unassembled indicator having a marker according to an exemplary embodiment.
Figure 5B:
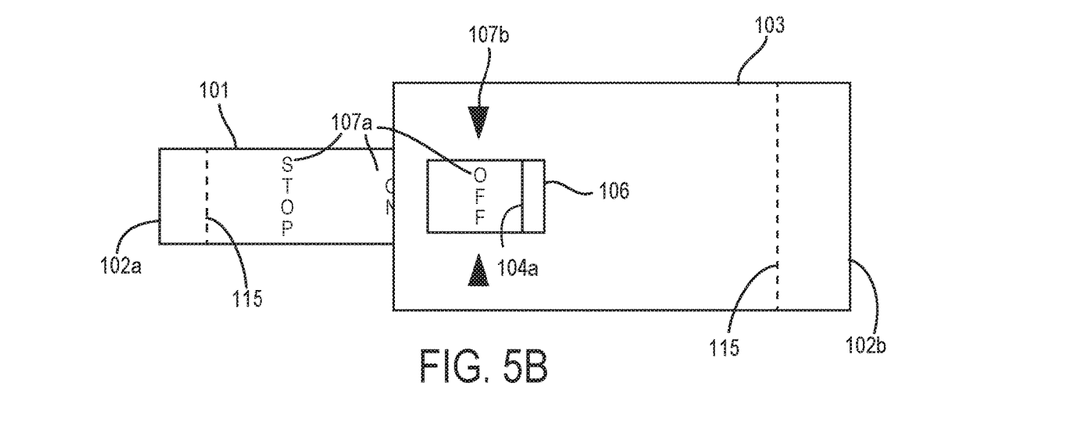
FIG. 5B is a top view of the assembled indicator of FIG. 5A in an initial configuration, according to an exemplary embodiment.
Figure 5C:
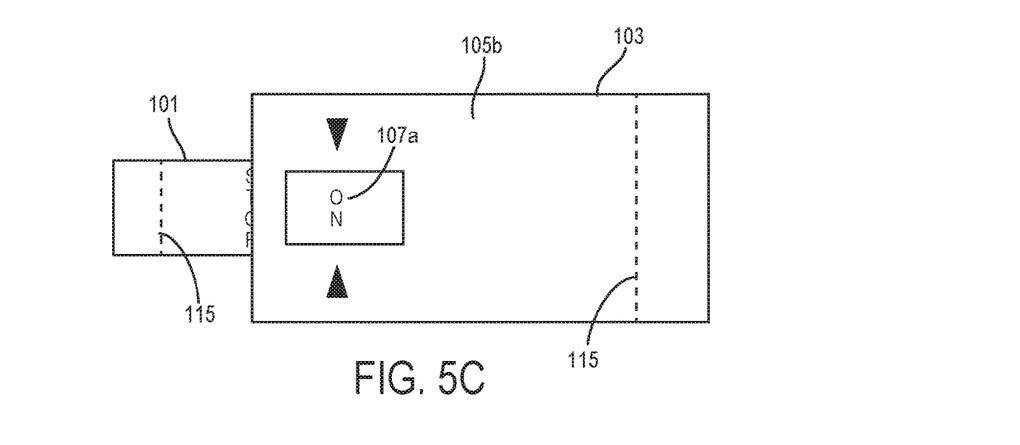
FIG. 5C is a top view of the assembled indicator of FIG. 5A in a second configuration, according to an exemplary embodiment.
Figure 6A:
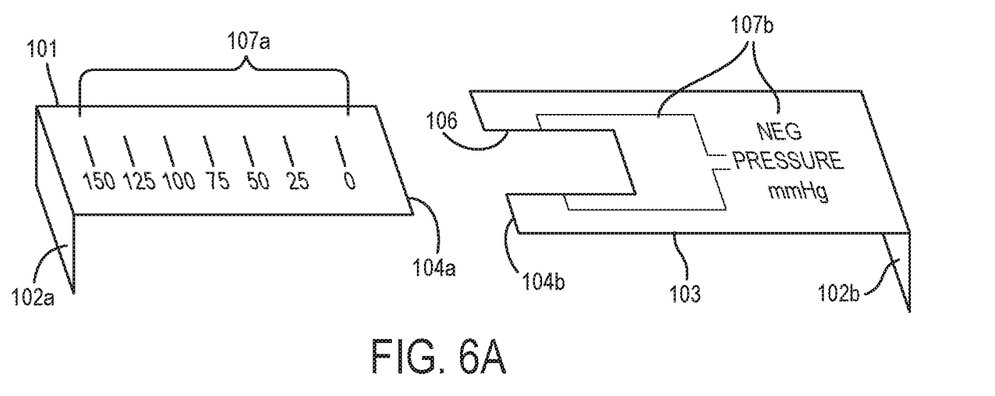
FIG. 6A is a top perspective view of an unassembled indicator having a marker according to an exemplary embodiment.
Figure 6B:
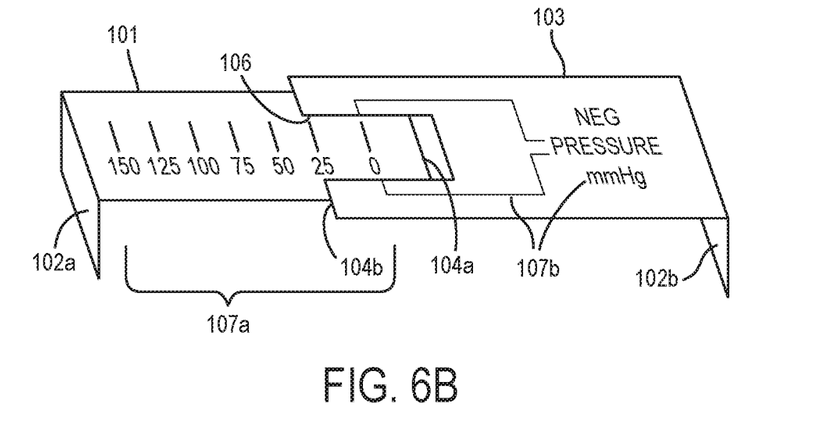
FIG. 6B is a top perspective view of the assembled indicator of FIG. 6A in an initial configuration, according to an exemplary embodiment.
Figure 6C:
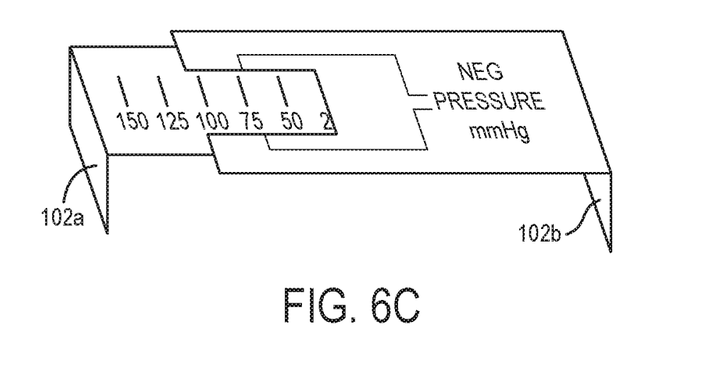
FIG. 6C is a top perspective view of the assembled indicator of FIG. 6A in a second configuration, according to an exemplary embodiment.

As illustrated in FIG. 5A-5C, in some embodiments, score lines or perforations 115 may optionally be provided along the indicator 100, allowing for the easy detachment of the indicator 100 from the wound dressing 20 in situations where a user wishes to remove the indicator 100 from the wound dressing 20.

The indictor 100 may be intended for single or multi-use, and can be made of any number of materials, such as, e.g. paperboard, cardboard, or plastic. The indicator 100 may be formed having any desired size or dimensions, with the dimensions and size of the indicator 100 generally corresponding to the dimensions and size of the wound dressing 20 with which the indicator 100 will be used.

In some embodiments, the first part 101 of the indicator 100 may have a length as defined between the attachment end 102a and the free end 104a is within a range of approximately 50 mm and approximately 100 mm, and more preferably within a range of approximately 60 mm and approximately 80 mm. In some embodiments, the second part 103 of the indicator 100 may have a length as defined between the attachment end 102b and the free end 104b within a range of approximately 40 mm and approximately 90 mm, and more preferably, between a range of approximately 50 mm and approximately 70 mm.

The wound dressing 20 and indicator 100 may be provided to a user as a combined unit, with the indicator 100 optionally being provided pre-attached to the wound dressing 20. In some embodiments, the pre-attached indicator 100 may be provided in a fully assembled and ready to use configuration. In other embodiments, the indicator 100 may be provided in a partially attached and/or partially assembled configuration, requiring additional assembly by the user prior to use. Alternatively, the indicator 100 may be provided separate from the wound dressing 20.

In embodiments in which the indicator 100 is provided separate from or only partially attached to the wound dressing 20, the wound dressing 20 may optionally include one or more visual or tactile markings that correspond to attachment point(s) for the unattached attachment ends 102a, 102b of the indicator 100. The indicator 100 may be attached to the wound dressing 20 prior to or subsequent to the attachment of the wound dressing 20 to the wound site.

In embodiments in which the indicator 100 is provided separate or only partially attached to the wound dressing 20, one or both of the first and second parts 101, 103 may be provided in a flat, unfolded configuration, such that, upon assembly the attachment ends 102a, 102b of the first and second parts 101, 103 are bent are folded by the user to assemble the indicator. In embodiments where a score line of perforations 115 are included in the indicator, such as e.g. shown in FIGS. 5A-5C, the score line or perforations 115 may be arranged at locations about the first and second parts 101, 103 to facilitate the assembly of the indicator 100.

The various indicator 100 configurations, indicator 100 attachment arrangements, and/or marker 107 designs and arrangements described herein and in the FIGS. are not intended to be limiting, and any other number of indicator 100 configurations, indicator 100 attachment arrangements, and/or marker 107 designs may be used to provide a user with an enhanced visualization of the collapse of a three-dimensional foam-based wound dressing 20 or the amount of negative pressure applied during a NPWT treatment.

For example, in some embodiments, the first and second parts of the indicator may be arranged to be parallel, but not collinear with one another. In other embodiments, the first and second parts of the indicator may be arranged to be non-parallel (e.g. perpendicular) relative to one another.

In some embodiments, the attachment end of one of the first or second parts may be attached at a location not corresponding to a position on the upper surface or the sidewall of the three-dimensional wound dressing structure (e.g. along the margin of the wound dressing), such that, upon collapse of the wound dressing, only one of the free ends of the indictor moves while the other free end remains stationary.

In some embodiments, the indicator is formed of only a single part. For example, in one embodiment, when the wound dressing is in an initial, uncompressed state, the free end of the single part may be aligned with a lateral side and/or top end of the upper surface of the three-dimensional structure of the wound dressing. Upon application of negative pressure, the displacement between the free end of the indicator and the inwardly translated lateral side and/or top end may provide the user with a visual indication of the collapse of the wound dressing.

In yet other embodiments of an indicator formed of only a single part, one or more markers may be formed about and arranged along the wound dressing (e.g. along the upper surfaces of one or both of the backing layer or foam layer), such that upon collapse of the wound dressing, the displacement of the marker relative to the indicator and/or the displacement of the indicator relative to the marker may alert a user to the collapse of the wound dressing.

As an alternative to, or in addition to coupling an indicator to the upper surface of the wound dressing, in some embodiments the indicator may be positioned between the foam layer and the backing layer. In such embodiments it may be desirable to position a rigid support entirely or at least partially between the lower surface of the backing layer and the upper surface of the foam layer so as to minimize the risk that the increasingly closer contact between the backing layer and foam layer as negative pressure is applied to the wound dressing does not inhibit movement of the first and second parts of the indicator relative to one another.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed:

1. A negative pressure wound therapy system comprising:
   a wound dressing sealable to a patient's skin surrounding a wound and configured to laterally collapse upon application of negative pressure to the wound dressing; and
   an indicator coupled to the wound dressing and configured to visually indicate an amount by which the wound dressing laterally collapses upon the application of negative pressure, the indicator comprising:
      a first part coupled to a first lateral side of the wound dressing, and
      a second part coupled to a second lateral side of the wound dressing opposite the first lateral side.

2. The negative pressure wound therapy system of claim 1, wherein:
   the amount by which the wound dressing laterally collapses is an amount by which a distance between the first lateral side and the second lateral side decreases upon the application of negative pressure.

3. The negative pressure wound therapy system of claim 1, wherein the first and second parts of the indicator extend along a top surface of the wound dressing and at least partially overlap with each other along the top surface.

4. The negative pressure wound therapy system of claim 1, wherein the first and second parts of the indicator are slidably connected along a top surface of the wound dressing such that the first part slides under or into the second part when the wound dressing laterally collapses.

5. The negative pressure wound therapy system of claim 4, wherein: the first part of the indicator comprises a marker on a top surface of the first part; and the second part of the indicator comprises a window through which the marker is at least partially visible when the first part slides under or into the second part.

6. The negative pressure wound therapy system of claim 5, wherein an edge of the window is collinear with an edge of the second part of the indicator such that the window forms a notch extending into the second part from the edge.

7. The negative pressure wound therapy system of claim 5, wherein the first and second parts of the indicator are configured to move relative to each other as the wound dressing laterally collapses such that a different portion of the marker is visible through the window based on an amount by which the wound dressing has laterally collapsed.

8. The negative pressure wound therapy system of claim 5, wherein: the marker comprises a colored scale having a plurality of colored bands; and one or more of the colored bands are visible through the window based on an amount by which the wound dressing has laterally collapsed.

9. The negative pressure wound therapy system of claim 8, wherein each of the colored bands corresponds to an amount of negative pressure and indicates the amount by which the wound dressing laterally collapses when the corresponding amount of negative pressure is applied to the wound dressing.

10. The negative pressure wound therapy system of claim 5, wherein:
the marker comprises a plurality of lines of text; and
one or more of the lines of text are visible through the window based on an amount by which the wound dressing has laterally collapsed.

11. The negative pressure wound therapy system of claim 5, wherein:
the marker comprises a gradient of lines; and
one or more of the lines are visible through the window based on an amount by which the wound dressing has laterally collapsed.

12. The negative pressure wound therapy system of claim 5, wherein:
the marker comprises a triangular shape; and
a different portion of the triangular shape is visible through the window based on an amount by which the wound dressing has laterally collapsed.

13. The negative pressure wound therapy system of claim 1, wherein the wound dressing comprises:
a foam layer having a first side and a second wound-facing side; and
a backing layer having a first side and a second wound-facing side abutting the first side of the foam layer, wherein the backing layer is substantially impermeable to air and configured to maintain the negative pressure applied to the wound dressing.

14. The negative pressure wound therapy system of claim 13, wherein the indicator is positioned between the foam layer and the backing layer.

15. The negative pressure wound therapy system of claim 13, wherein the indicator is coupled to the first side of the backing layer such that the backing layer is positioned between the indicator and the foam layer.

16. A method for monitoring a status of a negative pressure wound therapy treatment comprising:
applying a wound dressing to a patient's skin surrounding a wound, the wound dressing including an indicator configured to indicate to a user whether there has been a change in at least one of a lateral or a longitudinal dimension of the wound dressing, the indicator comprising:
a first part coupled to a first lateral side of the wound dressing, and
a second part coupled to a second lateral side of the wound dressing opposite the first lateral side;
applying a source of negative pressure to the wound dressing; and
observing, on the indicator, a change in at least one of the lateral or the longitudinal dimensions of the wound dressing.

17. The method of claim 16, wherein the wound dressing is configured to collapse in at least a lateral direction such that a second lateral dimension of the wound dressing following the application of negative pressure to the wound dressing is less than a first lateral dimension of the wound dressing prior to the application of negative pressure to the wound dressing.

18. The method of claim 16, wherein observing the change in at least one of the lateral or the longitudinal dimensions of the wound dressing comprises monitoring movement of one or both of the first part or the second part of the indicator following the application of negative pressure to the wound dressing.

19. The method of claim 18, wherein the monitoring of movement of one or both of the first part or the second part of the indicator is configured to indicate a collapse of the wound dressing in the lateral direction.

20. The method of claim 18, wherein a lack of movement of one or both of the first part or the second part of the indicator in response to the application of negative pressure is configured to indicate an issue with the negative pressure wound therapy treatment.

21. The method of claim 20, further comprising verifying a connection between the wound dressing and a pressure source configured apply a negative pressure to the wound dressing in response to no movement of either the first part or the second part of the indicator being observed.

* * * * *